United States Patent [19]

Takahashi et al.

[11] Patent Number: 5,493,063
[45] Date of Patent: Feb. 20, 1996

[54] PROCESS FOR OPTICAL RESOLUTION OF 1,2-DIOL DERIVATIVES

[75] Inventors: Eisaku Takahashi, Tokyo; Takashi Kimura, Uji; Satoru Kumazawa, Iwaki, all of Japan

[73] Assignee: Kureha Kagaku Kogyo K.K., Tokyo, Japan

[21] Appl. No.: 345,463

[22] Filed: Nov. 21, 1994

[30] Foreign Application Priority Data

Nov. 26, 1993 [JP] Japan .................................. 5-321082

[51] Int. Cl.$^6$ .......................... C07C 27/00; C07C 27/02
[52] U.S. Cl. ............................................ 568/858; 546/262
[58] Field of Search ............................. 568/858; 548/262

[56] References Cited

U.S. PATENT DOCUMENTS 4,855,438  8/1989  Kaulen et al. ........................ 548/262

FOREIGN PATENT DOCUMENTS 3-53886  3/1991  Japan .

OTHER PUBLICATIONS

"The Enantiomers of the Azole Fungicide HWG–1608–Asymmetric Synthesis of a 2-Hydroxyethyl Azole Fungicide", Johannes Kaulen, Angew. Chem. Int. Ed. Engl. vol. 28, pp. 462–463, 1989.

Primary Examiner—Werren B. Lone
Attorney, Agent, or Firm—Lowe, Price, Leblanc & Becker

[57] ABSTRACT

This invention provides a process for producing an optically active 1,2-diol derivative by optical resolution. The optically active 1,2-diol derivative of the formula (I) which is capable of utilizing as an intermediate of fungicidal optically-active azole derivatives can be produced by esterifying a 1,2-diol derivative of the formula (I) as a substrate with a carboxylic acid derivative of the formula (II) as a reagent in the presence of a lipase as a catalyst.

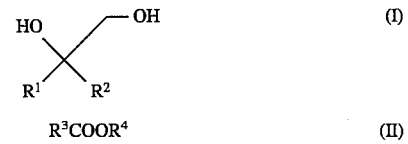

wherein $R^1$ is C1–C5 alkyl group, C3–C7 cycloalkyl group or C1–C5 haloalkyl group, $R^2$ is C1–C3 alkyl group substituted by a phenyl group which may have one or two halogen atoms and/or C1–C4 alkyl groups, C2–C3 alkenyl group substituted by a phenyl group which may have one or two halogen atoms and/or C1–C4 alkyl groups, or C1–C3 alkyl group substituted by a phenoxy group which may have one or two halogen atoms and/or C1–C4 alkyl groups, $R^3$ is C1–C10 alkyl group or aryl group, and $R^4$ is hydrogen atom, C1–C5 alkyl group, C2–C4 alkenyl group or $COR_3$.

8 Claims, No Drawings

PROCESS FOR OPTICAL RESOLUTION OF 1,2-DIOL DERIVATIVES

BACKGROUND OF THE INVENTION

1. Field of the Invention

The present invention relates to a process for production of optically active compounds, which are capable of utilizing as intermediates of fungicidal optically-active azole derivatives, by optical resolution by means of a lipase.

2. Description of the Related Arts

U.S. Pat. Nos. 4,855,438 and Angew. Chem. Int. Ed. Engl. 28, 462–463 (1989) disclose a process for asymmetric synthesis of (S)-2-[2-(4-chlorophenyl)ethyl]-3,3-dimethyl-1,2-butanediol which is an intermediate of (S)- α-[2-(4-chlorophenyl)ethyl]-α-(1,1-dimethylethyl)-1H-1,2,4-triazole- 1-ethanol having a higher fungicidal activity in enantiomers of optical isomers.

Japanese Patent Application Laid-Open No. 53886/1991 discloses optical resolution of 3-chloro-1,2-propanediol by means of a lipase.

The 1,2-diol used as a substrate for optical resolution by means of a lipase, which is described in the above-mentioned Japanese Patent Application Laid-Open No. 53886/1991, has a hydroxyl group attached to a primary carbon atom and a hydroxyl group attached to a secondary carbon atom.

On the other hand, (S)-2-[2-(4-chlorophenyl)ethyl]- 3,3-dimethyl-1,2-butanediol described in the above-mentioned U.S. Pat. No. 4,855,438 and Angew. Chem. Int. Ed. Engl. 28, 462–463 (1989) has a hydroxyl group attached to a primary carbon atom and a hydroxyl group attached to a tertiary carbon atom.

SUMMARY OF THE INVENTION

An object of the present invention is to provide a process for producing optically active 1,2-diol derivatives of the following formula (I) by optical resolution of 1,2-diol derivatives represented by the formula (I) which have a hydroxyl group attached to a primary carbon atom and a hydroxyl group attached to a tertiary carbon atom, as a substrate, which comprises utilizing an esterification reaction in the presence of a lipase as a catalyst.

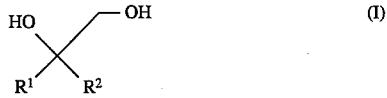
(I)

wherein $R^1$ is C1–C5 alkyl group, C3–C7 cycloalkyl group or C1–C5 haloalkyl group, $R^2$ is C1–C3 alkyl group substituted by a phenyl group which may have one or two halogen atoms and/or C1–C4 alkyl groups, C2–C3 alkenyl group substituted by a phenyl group which may have one or two halogen atoms and/or C1–C4 alkyl groups, or C1–C3 alkyl group substituted by a phenoxy group which may have one or two halogen atoms and/or C1–C4 alkyl groups.

As a result of earnest studies, the present inventors have found that an optically active 1,2-diol derivative of the formula (I) can be obtained by esterifying a 1,2-diol derivative of the above-mentioned formula (I) as the substrate with a carboxylic acid derivative of the following formula (II) as a reagent in the presence of a lipase as the catalyst, and thus the present invention is completed.

$$R^3COOR^4 \quad (II)$$

wherein $R^3$ is C1–C10 alkyl group or aryl group, $R^4$ is hydrogen atom, C1–C5 alkyl group, C2–C4 alkenyl group or $COR_3$.

The optically active 1,2-diol derivatives represented by the formula (I) which are obtained by the present invention can be introduced into fungicidal optically-active azole derivatives by replacing the hydroxyl group attaced to the primary carbon atom by 1H-imidazole or 1H-1,2,4-triazole according to a well known process.

DETAILED DESCRIPTION OF PREFERRED EMBODIMENTS

In the following, the present invention will be described in greater detail.

The present invention relates to a process for producing an optically active 1,2-diol derivative of the above mentioned formula (I) by optical resolution which comprises esterifying a 1,2-diol derivative of the above mentioned formula (I) as the substrate with a carboxylic acid derivative of the above mentioned formula (II) in the presence of a lipase as the catalyst.

$R^1$ includes 1,1-dimetylethyl group and 1,1-dimethylpropyl group.

In the definition of R1, the term "C1–C5 haloalkyl group" means C1–C5 alkyl group in which one or more hydrogen atoms are each substituted with a halogen atom (preferably fluorine atom).

$R^2$ includes 2-(4-chlorophenyl)ethyl group, 2-(2,4-dichlorophenyl)ethyl group, 2-(4-methylphenyl)ethyl group, 2-(4-chlorophenyl)ethenyl group and (4-chlorophenoxy)methyl group.

In $R^3$, preferable examples include C1–C5 alkyl group and phenyl group which may be substituted with one or more selected from halogen atoms, C1–C3 alkyl groups and C1–C3 alkoxy groups In $R^4$, preferable examples include C2–C3 alkenyl group and $COR_3$.

An amount of the carboxylic acid derivative of the formula (II) to be used, expressed as a molar ratio relative to the 1,2-diol derivative of the formula (I), is preferably in a range of 1:0.5–1:30, and more preferably in a range of 1:0.9–1:15.

The lipase which is used in the present invention may be either one which is produced by microorganism or one which originates from an animal or plant.

The term "lipase" used herein is a broad meaning of lipase, including esterase.

In the present invention, the lipase may be used in one of various forms such as a purified enzyme, a crude enzyme, an enzyme-containing substance, a cultured liquor of a microorganism, a cultured substance, microorganisms, a cultured filtrate, or a treated product thereof.

Also, the enzyme can be used in combination with microorganisms.

Specific examples of the microorganisms which produce the lipase include, for instance, microorganisms belonging to the genus Enterobacter, the genus Arthrobacter, the genus Brevibacterium, the genus Pseudomonas, the genus Alcaligenes, the genus Micrococcus, the genus Chromobacterium, the genus Microbacterium, the genus Corynebacterium, the genus Bacillus, the genus Lactobacillus, the genus Trichoderma, the genus Candida, the genus Saccharomyces, the genus Rhodotorula, the genus Cryptococcus, the genus Torulopsis, the genus Pichia, the genus Penicillium, the genus Aspergillus, the genus Rhizopus, the genus Mucor, the genus Aureobasidium, the genus Actinomucor, the genus Nocardia, the genus Streptomyces, the genus Hansenula, and the genus Achromobacter.

The cultures of the above enumerated microorganisms are generally carried out in a conventional manner; for example, the enzyme can be obtained by a liquid culturing.

For example, a microorganism is inoculated into a sterilized liquid medium, e.g., a malt extract-yeast extract medium (5 g of peptone, 10 g of glucose, 3 g of yeast extract and 3 g of a malt extract are dissolved in 1 liter of water, and the pH is adjusted to 6.5) for a fungi or an yeast, or a nutrient broth medium supplemented with glucose (10 g of glucose, 5 g of peptone, 5 g of meat extract, and 8 g of NaCl are dissolved in 1 liter of water, and the pH is adjusted to 7.2) for bacteria, and shaking culture is carried out usually at 20° to 40° C. for 1 to 8 days. If necessary, solid culture may be carried out.

Among the lipases originating from these microorganisms, several lipases are commercially available and, thus, readily obtainable. Examples of commercially available lipases include the lipase originating from the genus Pseudomonas [Lipase P, (manufactured by Amano Seiyaku)], the lipase originating from the genus Aspergillus [Lipase A, (manufactured by Amano Seiyaku)], the lipase originating from the genus Mucor [Lipase M, (manufactured by Amano Seiyaku)], the lipases originating from the genus Candida [Lipase AY, (manufactured by Amano Seiyaku) and Lipase MY (manufactured by Meito Sangyo Co., Ltd.)]. The lipase originating from the genus Alcaligenes [Lipase PL (manufactured by Meito Sangyo Co., Ltd.)], the lipase originating from the genus Achromobacter (manufactured by Shin-nippon Kagaku), the lipase originating from the genus Chromobacterium (manufactured by Toyo Jozo Co., Ltd.), the lipase originating from the genus Rhizopus [Talipase (manufactured by Tanabe Seiyaku Co., Ltd.)], the esterase originating from the genus Pseudomonas [Cholesterol esterase (manufactured by Toyo Jozo Co., Ltd.)], and the like.

Examples of animal- or plant-originating lipases include steapsin, pancreatin, pig liver esterase, wheat malt esterase, etc.

Among them, the lipase originating from the genus Candida [Lipase AY (manufactured by Amano Seiyaku)] and the lipase originating from the genus Pseudomonas [Lipase Type XIII (manufactured by Sigma)] are preferable in terms of their reactivity and other aspects.

These lipases may be purified or in a state of crude products, and they can be used individually or can be mixed as occasion may demand.

They can also be used as immobilized enzymes or cells which are immobilized onto a resin, etc.

In this case, they can be used in the form of a powder or granule. For example, an immobilized lipase in which one of the above lipases is carried on and immobilized onto a macromolecule such as polystyrene, polypropylene, starch or gluten, or an inorganic material such as activated carbon, porous glass, celite, zeolite, kaolinite, bentonite, alumina, silica gel, hydroxyapatite, calcium phosphate or metal oxide, by a physical adsorption method, etc. is dried to be utilized.

After the reaction has been completed, the lipase recovered from the reaction liquor by filtration can be used repeatedly, because it has a sufficient reactivity and sufficient stereo-specificity. It is also possible to use for a continuous reaction.

In the present invention, aprotic organic solvents are preferably used as a reaction solvent. Examples of the solvent include C4–C7 alkanes, such as n-hexane and isopentane; C6–C8 cycloalkanes, such as cyclohexane and methylcyclohexane; C1–C2 haloalkanes, such as chloroform and 1,2-dichloroethane; C6–C9 aromatic hydrocarbons, such as benzene, toluene and xylene; C2–C4 alkyl ethers such as diethyl ether and diisopropyl ether; alicyclic ethers, such as tetrahydrofuran and tetrahydropyran; and others.

In the present invention, it is also possible to use a carboxylic acid derivative of the formula (II) as a reaction solvent without using these aprotic organic solvents.

The reaction temperature is preferably from 15° C. to the boiling point of the solvent used, and preferably from 30° to 45° C.

The reaction period of time is varied depending upon various factors, such as a) the type of the carboxylic acid derivative of the formula (II) used and the amount thereof relative to the 1,2-diol derivative of the formula (I), b) the type of lipase used and the amount thereof relative to the 1,2-diol derivative of the formula (I), c) the presence or absence of the solvent used, and d) the reaction temperature.

The amount of the lipase used can be determined depending upon the enzyme activity of the enzyme.

For example, it is preferably used in an amount of 0.01 to 10 times, more preferably 0.05 to 2 times of the weight of the substrate: 1,2-diol derivative of the formula (I). The reaction may be carried out with stirring, shaking or left standing, but preferably with stirring.

The 1,2-diol derivatives of the above mentioned formula (I) used as the substrate can be synthesized by converting the oxygen atom of a ketone compound (used as a starting material for oxirane compound described in U.S. Pat. No. 4,532,341) by a Wittig's reagent into a methylene group, followed by oxidizing a double bond to form a 1,2-diol.

The reaction operations of the present invention will now be specifically described.

In a reactor are weighed prescribed amounts of a 1,2-diol derivative of the formula (I), of a carboxylic acid ester of the formula (II) and of a lipase, and preferably an aprotic organic solvent such as toluene, benzene or chloroform is added thereto in a prescribed amount.

The reaction is then carried out at a given temperature, preferably with stirring or shaking.

The progress of the reaction is monitored by determining the reaction amount of the 1,2-diol derivative of the formula (I) by TLC or HPLC. When a prescribed amount has been reacted, the stirring or shaking is stopped, and the reaction mixture is allowed to stand, followed by filtration or centrifugal precipitation to remove the lipase.

The filtrate is concentrated in vacuo to obtain a reaction mixture containing an optically active 1,2-diol derivative of the formula (I).

From the optically active 1,2-diol derivative of the formula (I), an optically active fungicidal azole derivative can be derived via a step of sulfoesterification and a step of azolation.

When the optically active 1,2-diol derivative of the formula (I) is subjected to the subsequent steps, it can be used after being isolated or as it is in the reaction mixture.

Thus, the optically active 1,2-diol derivative of the formula (I) which is capable of utilizing as an intermidiate for optically acitive fungicidal azole derivatives can be obtained by optical resolution by esterifying the 1,2-diol derivative of the formula (I) as a substrate with a carboxylic acid derivative of the formula (II) as a reagent in the presence of lipase as a catalyst.

EXAMPLES

The present invention will now be described by referring to examples, but the present invention should not be restricted thereto unless the examples deviate from the spirits of the present invention.

REFERENTIAL EXAMPLE 1

Preparation of Immobilized Enzyme:

Into a 30 ml vial bottle equipped with a spigot was put 0.3 g of Amano AY (manufactured by Amano Seiyaku), then 10 ml of 5 mM potassium phosphate buffer (pH 7.0) and 3.0 g of celite powder [Hiflowsuper Cell(manufactured by Kanto Kagaku)] were added thereto, and the content was stirred at 4° C. for 15 minutes. The resulting enzyme immobilized and adsorbed on the cellite was spread over a Petri dish having a diameter of 90 mm, and dried in a vacuum desiccator for overnight and then in the presence of phosphorus pentoxide for 2 days.

REFERENTIAL EXAMPLE 2

Synthesis of 2-[2-(4-chlorophenyl)ethyl]-3,3-dimethyl-1,2-butanediol (1) Synthesis of 1-(4-chlorophenyl)-3-methylene-4,4-dimethylpentane 1.9 g of sodium hydride (obtained by washing 60% oily sodium hydride with anhydrous benzene) was added to 60 ml of anhydrous dimethylsulfoxide under a nitrogen atmosphere, followed by stirring at 70° C. for 30 mminutes. The mixture was cooled with iced-water, to which 27.9 g of methyltriphenylphosphonium bromide was added and stirred for 30 minutes while cooling with iced-water, followed by stirring at room temperature for 10 minutes.

After addition of 8.8 g of 1-(4-chlorophenyl)-4,4-dimethyl- 3-pentannone, the resulting mixture was allowed to react with stirring at room temperature for 1 hour and then at 50° C. for 30 minutes.

The reaction mixture was cooled and poured into iced-water, followed by extracting with hexane to separate an organic layer. After the separated organic layer was washed with a saline solution, it was dried with anhydrous sodium sulfate, and the solvent was removed by distillation. The resulting oily product was purified by column chromatography on a silica gel column to obtain 7.4 g of the target compound.

(2) Synthesis of 2-[2-(4-chlorophenyl)ethyl]-3,3-dimethyl-1,2-butanediol 3.0 g of 1-(4-chlorophenyl)-3-methylene-4,4-dimethylpentane prepared as described above (1) was dissolved in a mixture solvent of 40 ml of acetonitrile and 10 ml of water, and 3.2 g of 4-methylmorpholine-N-oxide was added thereto. After addition of 10 ml of a 4% aqueous solution of osmium tetroxide, the mixture was stirred at room temperature for 24 hours. After adding an aqueous solution of sodium hydrogen sulfite, the mixture was stirred for 1 hour, and insoluble substances were removed by filtration, and the filtrate was extracted with ethyl acetate. The separated organic layer was washed with water and dried, followed by removing the solvent under vaccum to obtain an oily product. It was then purified by column chromatography on a silica gel column to obtain 1.4 g of the target compound as a white solid.

NMR (CDCl$_3$+D$_2$O, ppm) δ: 0.95(s,9H), 1.65–1.95(m, 2H), 2.55– 2.88(m,2H), 3.55(d, 1H,J=10 Hz), 3.77(d, 1H,J= 10 Hz), 7.07(d,2H,J=8 Hz), 7.25(d,2H,J=8 Hz).

EXAMPLE 1

Optical resolution of 2-[2-(4-chlorophenyl)ethyl]-3,3-dimethyl-1,2-butanediol

Into a 10 ml vial bottle equipped with a spigot was put 50 mg of the celite absorbed and immobolized enzyme of Lipase AY (manufactured by Amano Seiyaku) prepared in Referential Example 1. Then, 50 mg of 2-[2-(4-chlorophenyl)ethyl] -3,3-dimethyl-1,2-butanediol (refer to as "1,2-butanediol" in this example) prepared in Referential Example 2, 224 mg of vinyl butyrate and 2 ml of toluene were added thereto, and the mixture was shaken at 37° C. for 150 hours.

After conclusion of the reaction, the amount of unreacted 1,2-butanediol was determined by high performance liquid chromatography [column condition: 5C18-AR produced from Nacarai Tesque (φ4.6 mm×150 mm), an aqueous 70% acetonitrile solution, 1.0 ml/min., detection wavelength: 268 nm].

Subsequently, the reaction solution was taken out, and the immobilized enzyme was removed by filtration under suction. The solvent and other impurities were then removed in vacccum.

The 1,2-butanediol and 1,2-butanediol monobutyrate contained in the residue were separated by column chromatography on silica gel (column condition: n-hexane/ethyl acetate=3/1).

As a result of analyzing the resultant 1,2-butanediol by high performance liquid chromatography (column: Chiralcell-OD manufactured by Daisel Chemical Co., Ltd., solvent: n-hexane/2-propanol=4/1), the yield of the (–)- 1,2-butanediol (85.0%ee) was 52.4%.

EXAMPLE 2

Optical resolution of 2-[2-(4-chlorophenyl)ethyl]-3,3-dimethyl-1,2-butanediol.

Into a 10 ml vial bottle equipped with a spigot was put 50 mg of the celite absorbed and immobolized enzyme of Lipase Type XIII (manufactured by Sigma) prepared in accordance with Referential Example 1. Then, 50 mg of 2-[2-( 4-chlorophenyl)ethyl]-3,3-dimethyl-1,2-butanediol (refer to as "1,2-butanediol" in this example) prepared in Referential Example 2, 224 mg of vinyl butyrate and 2 ml of toluene were added thereto, and the mixture was shaken at 37° C. for 150 hours.

After conclusion of the reaction, the amount of unreacted 1,2-butanediol was determined by high performance liquid chromatography [column condition: 5C18-AR produced from Nacarai Tesque (φ4.6 mm×150 mm), an aqueous 70% acetonitrile solution, 1.0 ml/min., detection wavelength: 268 nm].

Subsequently, the reaction solution was taken out and the immobilized enzyme was removed by filtration under suction. The solvent and other impurities were then removed in vacccum.

The 1,2-butanediol and 1,2-butanediol monobutyrate contained in the residue were separated by column chromatography on silica gel (column condition: n-hexane/ethyl acetate=3/1).

As a result of analyzing the resultant 1,2-butanediol by high performance liquid chromatography [column: Chiralcell-OD (φ4.6 mm×150 mm) manufactured by Daisel Chemical Co., Ltd., solvent: n-hexane/2-propanol= 4/1), 1.0 ml/min., detection wavelength: 268 nm], the yield of the (+)-1,2-butanediol (73.5%ee) was 48.5%.

What is claimed is:

1. A process for producing an optically active 1,2-diol derivative of the formula (I) by optical resolution which comprises esterifying a 1,2-diol derivative of the formula (I) as a substrate with a carboxylic acid derivative of the formula (II) as a reagent in the presence of a lipase as a catalyst,

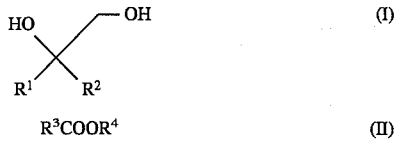

$$R^3COOR^4 \quad (II)$$

wherein $R^1$ is C1–C5 alkyl group, C3–C7 cycloalkyl group or C1–C5 haloalkyl group, $R^2$ is C1–C3 alkyl group substituted by a phenyl group which has one or two halogen atoms, one or two C1–C4 alkyl groups, or one halogen atom and one C1–C4 alkyl group, C2–C3 alkenyl group substituted by a phenyl group which has one or two halogen atoms, or one or two C-1–C4 alkyl groups, or one halogen atom and one C1–C4 alkyl groups, or C1–C3 alkyl group substituted by a phenoxy group which may have one or two halogen atoms, or one or two C1–C4 alkyl groups, or one halogen atom and one C1–C4 alkyl group, $R^3$ is C1–C10 alkyl group or aryl group, and $R^4$ is hydrogen atom, C1–C5 alkyl group, C2–C4 alkenyl group or $COR_3$, provided that said halogen does not include astitine.

2. The process for producing an optically active 1,2-diol derivative according to claim 1, wherein the optically active 1,2-diol derivative is (−)-2-[2-(4-chlorophenyl)ethyl]- 3,3-dimethyl-1,2-butanediol.

3. The process for producing an optically active 1,2-diol derivative according to claim 1, wherein the optically active 1,2-diol derivative is (+)-2-[2-(4-chlorophenyl)ethyl] -3,3-dimethyl-1,2-butanediol.

4. The process for producing an optically active 1,2-diol derivative according to claim 1, wherein the lipase is a lipase originating from the genus Candida or the genus Pseudomonas.

5. A process for producing an optically active 1,2-diol derivative of the formula (I) by optical resolution according to claim 1, wherein $R^2$ is C1–C3 alkyl group substituted by a phenyl group which may have one chlorine, two chlorines or one C1–C4 alkyl group, C2–C3 alkenyl group substituted by a phenyl group which may have one chlorine, two chlorines or one C1–C4 alkyl group, or C1–C3 alkyl group substituted by a phenoxy group which may have one chlorine, two chlorines or one C1–C4 alkyl group.

6. The process for producing an optically active 1,2-diol derivative according to claim 5, wherein the optically active 1,2-diol derivative is (−)-2-[2-(4-chlorophenyl) ethyl]-3,3-dimethyl- 1,2-butanediol.

7. The process for producing an optically active 1,2-diol derivative according to claim 5, wherein the optically active 1,2-diol derivative is (+)-2-[2-(4-chlorophenyl) ethyl]-3,3-dimethyl- 1,2-butanediol.

8. The process for producing an optically active 1,2-diol derivative according to claim 5, wherein the lipase is a lipase originating from the genus Candida or the genus Pseudomonas.

* * * * *